United States Patent
Heckenberger et al.

(10) Patent No.: US 9,962,456 B2
(45) Date of Patent: May 8, 2018

(54) DEVICE FOR DISINFECTING, STERILIZING AND/OR MAINTAINING MEDICAL, ESPECIALLY DENTAL, INSTRUMENTS

(75) Inventors: Hans Heckenberger, Assmannshardt (DE); Hans-Dieter Wiek, Hochdorf (DE); Bernd Gugel, Ulm (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 1254 days.

(21) Appl. No.: 13/522,917

(22) PCT Filed: Feb. 17, 2011

(86) PCT No.: PCT/EP2011/052326
§ 371 (c)(1),
(2), (4) Date: Aug. 13, 2012

(87) PCT Pub. No.: WO2011/101396
PCT Pub. Date: Aug. 25, 2011

(65) Prior Publication Data
US 2012/0298151 A1     Nov. 29, 2012

(30) Foreign Application Priority Data
Feb. 17, 2010   (DE) .................. 10 2010 002 038

(51) Int. Cl.
*A61L 2/07*   (2006.01)
*A61L 2/24*   (2006.01)
(Continued)

(52) U.S. Cl.
CPC .................. *A61L 2/07* (2013.01); *A61L 2/24* (2013.01); *B05B 7/1272* (2013.01);
(Continued)

(58) Field of Classification Search
CPC ......... A61B 19/34; A61B 19/343; A61L 2/07; A61C 19/002
See application file for complete search history.

(56) References Cited

U.S. PATENT DOCUMENTS 5,197,499 A * 3/1993 Bodenmiller ............. A61L 2/04
134/102.3
5,380,369 A * 1/1995 Steinhauser ............. A61L 2/025
134/1
(Continued)

FOREIGN PATENT DOCUMENTS

DE     4323815 A1    1/1995
DE    19721538 A1   11/1998
(Continued)

OTHER PUBLICATIONS

NL1004670—Abstract, Apr. 1997.*
International Search Report for PCT/EP2011/052326 dated Apr. 15, 2011.

*Primary Examiner* — Marc Lorenzi
(74) *Attorney, Agent, or Firm* — Marshall, Gerstein & Borun LLP

(57) ABSTRACT

A device for disinfecting, sterilizing and/or maintaining medical, especially dental, instruments comprises a maintenance and cleaning chamber for accommodating instruments to be conditioned and means for supplying different cleaning or maintenance media for cleaning, disinfecting or sterilizing and/or maintaining the instruments in subsequent steps. The start times of the conditioning cycles for the different instruments are staggered.

4 Claims, 10 Drawing Sheets

(51) Int. Cl.
*B05B 7/12* (2006.01)
*B05B 7/24* (2006.01)
*B65D 83/26* (2006.01)
*B65D 83/62* (2006.01)

(52) U.S. Cl.
CPC ......... *B05B 7/2494* (2013.01); *A61L 2202/17* (2013.01); *B65D 83/262* (2013.01); *B65D 83/62* (2013.01)

(56) References Cited

U.S. PATENT DOCUMENTS

| | | | | |
|---|---|---|---|---|
| 5,571,488 A | * | 11/1996 | Beerstecher | A61B 19/34 |
| | | | | 134/94.1 |
| 5,723,090 A | | 3/1998 | Beerstecher et al. | |
| 6,368,556 B1 | * | 4/2002 | Morgenstjerne | A61C 19/002 |
| | | | | 134/102.2 |
| 2002/0068029 A1 | * | 6/2002 | Johansen | A61C 19/002 |
| | | | | 422/297 |
| 2006/0104875 A1 | * | 5/2006 | Lund-Jensen | A61C 19/002 |
| | | | | 422/297 |
| 2007/0031778 A1 | | 2/2007 | Helfenbein et al. | |
| 2010/0151415 A1 | * | 6/2010 | Wiek | A61C 19/002 |
| | | | | 433/104 |
| 2011/0206555 A1 | | 8/2011 | Wiek et al. | |

FOREIGN PATENT DOCUMENTS

| | | | | |
|---|---|---|---|---|
| DE | 102008020586 A1 | 10/2009 | | |
| EP | 1749502 A1 | 2/2007 | | |
| NL | 1004670 C1 * | 4/1997 | ............ | A61C 19/002 |
| WO | WO 2008138645 A2 * | 11/2008 | ............ | A61C 1/0084 |

\* cited by examiner

| | QUATTROcare plus | | | | | | | | | | | | | | | | | | | | | |
|---|---|---|---|---|---|---|---|---|---|---|---|---|---|---|---|---|---|---|---|---|---|---|
| | time sequence | | | | | | | | | | | | | | | | | | | | | |
| Instrument 1 | Internal cleaning | | | | | | | | | | | | | | | | | | | | | |
| | Period of action | | | | | | | | | | | | | | | | | | | | | |
| | Oil maintenance | | | | | | | | | | | | | | | | | | | | | |
| | Blowing air through | | | | | | | | | | | | | | | | | | | | | |
| Instrument 2 | Internal cleaning | | | | | | | | | | | | | | | | | | | | | |
| | Period of action | | | | | | | | | | | | | | | | | | | | | |
| | Oil maintenance | | | | | | | | | | | | | | | | | | | | | |
| | Blowing air through | | | | | | | | | | | | | | | | | | | | | |
| Instrument 3 | Internal cleaning | | | | | | | | | | | | | | | | | | | | | |
| | Period of action | | | | | | | | | | | | | | | | | | | | | |
| | Oil maintenance | | | | | | | | | | | | | | | | | | | | | |
| | Blowing air through | | | | | | | | | | | | | | | | | | | | | |
| Instrument 4 | Internal cleaning | | | | | | | | | | | | | | | | | | | | | |
| | Period of action | | | | | | | | | | | | | | | | | | | | | |
| | Oil maintenance | | | | | | | | | | | | | | | | | | | | | |
| | Blowing air through | | | | | | | | | | | | | | | | | | | | | |
| | | | | | Cleaning spray KaVo CLEANspray | | | | | | | | | | | | | | | | | |
| | | | | | Period of action of the KaVo CLEANspray (>1min) | | | | | | | | | | | | | | | | | |
| | | | | | Oil maintenance spray QUATTROcare plus | | | | | | | | | | | | | | | | | |
| | | | | | Blowing out with compressed air (30sec) | | | | | | | | | | | | | | | | | |

Fig. 2

|  |  | QUATTROcare dis-chem. time sequence |
|---|---|---|

| Instrument 1 | Internal cleaning |
|---|---|
|  | Period of action |
|  | Disinfection |
|  | Period of action |
|  | Oil maintenance |
|  | Blowing air through |
| Instrument 2 | Internal cleaning |
|  | Period of action |
|  | Disinfection |
|  | Period of action |
|  | Oil maintenance |
|  | Blowing air through |
| Instrument 3 | Internal cleaning |
|  | Period of action |
|  | Disinfection |
|  | Period of action |
|  | Oil maintenance |
|  | Blowing air through |
| Instrument 4 | Internal cleaning |
|  | Period of action |
|  | Disinfection |
|  | Period of action |
|  | Oil maintenance |
|  | Blowing air through |

Cleaning spray KaVo CLEANspray
Period of action of the KaVo CLEANspray (>1min)
Oil maintenance spray QUATTROcare plus
Blowing out with compressed air (30sec)
Disinfectant spray (3sec)
Period of action of the disinfectant spray (>2min)

Fig. 4

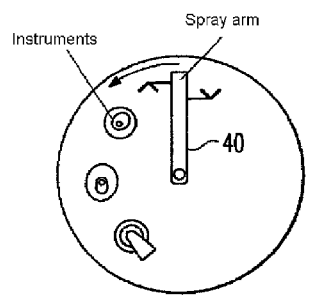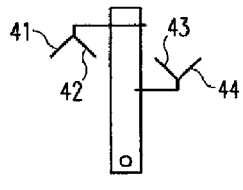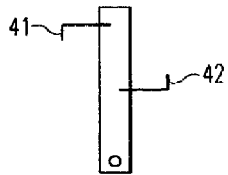
Fig. 8a    Fig. 8b    Fig. 8c
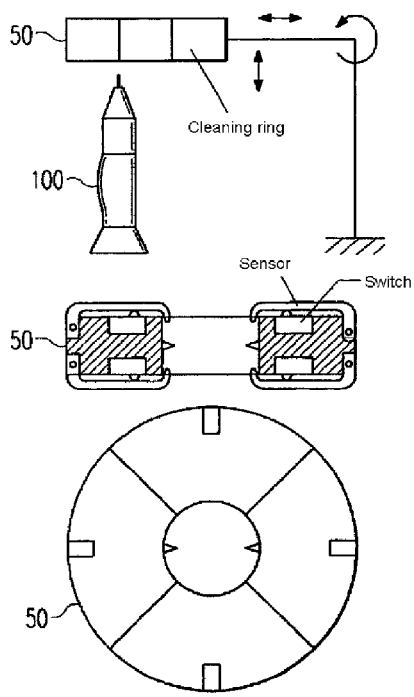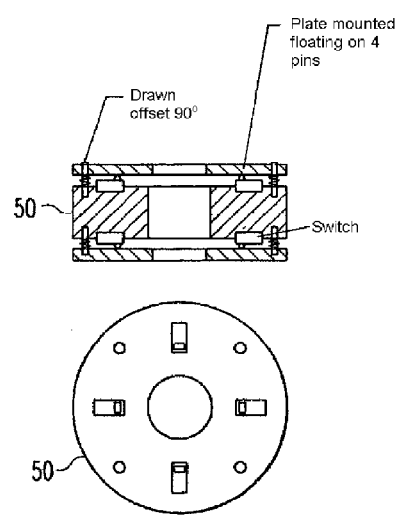
Fig. 9    Fig. 10

DEVICE FOR DISINFECTING, STERILIZING AND/OR MAINTAINING MEDICAL, ESPECIALLY DENTAL, INSTRUMENTS

BACKGROUND OF THE INVENTION

Field of the Invention

The present invention relates to a device which is provided for disinfecting, sterilizing and/or maintaining medical instruments. In particular, dental instruments are to be conditioned with the device.

Related Technology

Medical or dental handpieces are tubular parts which the doctor holds as a handle during treatment. A handpiece conventionally used in dental practice is a so-called drill handpiece, which carries a treatment tool, in particular a drill, at its forward end and is coupled at its rear end to a supply hose by means of a coupling. Supply lines for power for driving the treatment instrument, as well as fluid lines for treatment media, for example air and/or water, extend through the handpiece. A distinction is often made between so-called turbine handpieces, in which compressed air is provided for supplying a turbine arranged in the forward end region, and so-called motor handpieces, which have an electric motor as the drive unit.

In order to maintain the function of the handpieces, maintenance, in particular of the rotatably mounted drive elements, is required from time to time. Furthermore, ever increasing hygiene demands in dental practice mean that handpieces have to be conditioned at regular intervals. Successful conditioning and compliance with the corresponding requirements must be fully documented by the dentist, which involves a not inconsiderable outlay in terms of personnel and organization.

Manual reconditioning of dental handpieces has hitherto been carried out by first disinfecting the instruments by spraying and washing them externally after use on a patient. Cleaning of the interior of the instruments, on the other hand, was generally not carried out. In the meantime, however, cleaning and disinfecting devices in which the instruments are conditioned before being subjected to maintenance with oil have become available on the market. Machine conditioning has clear advantages over manual maintenance of the instruments, because only a machine process permits reliable and reproducible cleaning and maintenance.

However, the devices known hitherto can generally be used only for individual conditioning steps, so that cleaning, maintenance and sterilization must each be carried out separately. All the devices required therefor take up a relatively large amount of space, and electrical, pneumatic and fluid connections are required for each of the devices. Consequently, the performance of a complete machine conditioning of dental instruments by means of individual devices is very laborious and is associated with a high outlay in terms of cost.

A further disadvantage is that the individual devices are generally not linked with one another, so that there can be no exchange of data between the devices. This in turn leads to extra work for the operating personnel, because it is not possible to prepare fully automatic documentation of instrument conditioning. Furthermore, the instruments must be moved manually from device to device in intermediate steps, which is associated with intensive personnel use and a large time requirement.

SUMMARY OF THE INVENTION

The object underlying the present invention is, therefore, to provide a novel device for disinfecting, sterilizing and/or maintaining, or generally for conditioning, medical, especially dental, instruments, with which the disadvantages mentioned above are avoided.

Accordingly, there is proposed according to the invention a device for disinfecting, sterilizing and/or maintaining medical, especially dental, instruments, which has a maintenance and cleaning chamber for receiving instruments that are to be conditioned as well as means for supplying different cleaning or maintenance media for cleaning, disinfecting or sterilizing and/or maintaining the instruments in successive steps. It is provided according to the invention that the start times for the conditioning cycles for the different instruments are staggered.

The procedure according to the invention has the result that the media required for the conditioning of the instruments do not have to be supplied to a plurality of instruments at the same time. This allows the amount of medium to be metered precisely in each case. At the same time, however, the time sequence of the conditioning of all the instruments can be staggered because the conditioning cycles overlap in terms of time. Ultimately, a device is thereby created with which all the steps required for the conditioning of an instrument can be carried out while at the same time the quality of the conditioning is very high owing to the possibility of precise metering of the media, and on the other hand the conditioning of a plurality of instruments takes a comparatively small amount of time.

According to a first preferred embodiment of the present invention, cleaning and disinfection of the instruments is carried out by means of superheated steam. In this case it is provided that a conditioning cycle for an instrument consists in each case of six successive steps, namely internal cleaning by means of superheated steam, external cleaning by means of superheated steam, disinfection by means of superheated steam, oil maintenance by means of oil-containing compressed air, blowing compressed air through, and further external cleaning by means of superheated steam. A conditioning cycle for an instrument is preferably started when the preceding instrument is being maintained by means of oil-containing compressed air.

In a second preferred embodiment, disinfection of the instruments is carried out by supplying a disinfectant, in particular a spray, and allowing it to act, the period of action increasing for subsequent instruments. A conditioning cycle for an instrument preferably consists in this case of the following steps: internal cleaning by supplying a cleaning agent and allowing it to act, disinfection by supplying a disinfectant and allowing it to act, oil maintenance by supplying an oil maintenance agent, and blowing air through the instrument.

In a third preferred embodiment, internal cleaning of the instruments is carried out by supplying a cleaning agent, in particular a cleaning spray, and allowing it to act, the period of action increasing for the subsequent instruments. A conditioning cycle for an instrument preferably consists in this case of the following steps: internal cleaning by supplying a cleaning agent and allowing it to act, oil maintenance by supplying an oil maintenance agent, and blowing compressed air through the instrument. In the variant just described and in the variant mentioned above, a conditioning cycle for an instrument is preferably started when the period of action for the cleaning agent for the preceding instrument begins.

According to another advantageous further development of the invention, it can further be provided that, prior to the supply of the cleaning or maintenance media, the instruments are flushed with cold water under a high pulsed pressure. It has been shown that, as a result of this measure, which can also be used independently of the above-described inventive idea, particularly effective cleaning of the instruments is possible.

Ultimately, therefore, a device is proposed which allows especially dental instruments to be conditioned in a fully automatic, reliable and reproducible manner.

BRIEF DESCRIPTION OF THE DRAWINGS

The invention is to be explained in greater detail below by means of the accompanying drawing, in which:

FIG. 2 shows the time sequence of the reconditioning of four instruments in the embodiment of FIG. 1;

FIG. 4 shows the time sequence of the reconditioning of four instruments in the embodiment of FIG. 3;

FIGS. 8a to 8c show views of a spray arm for supplying superheated steam;

FIGS. 9 and 10 show views of a preferred annular arrangement of nozzles for applying superheated steam.

DETAILED DESCRIPTION

Figure 1:
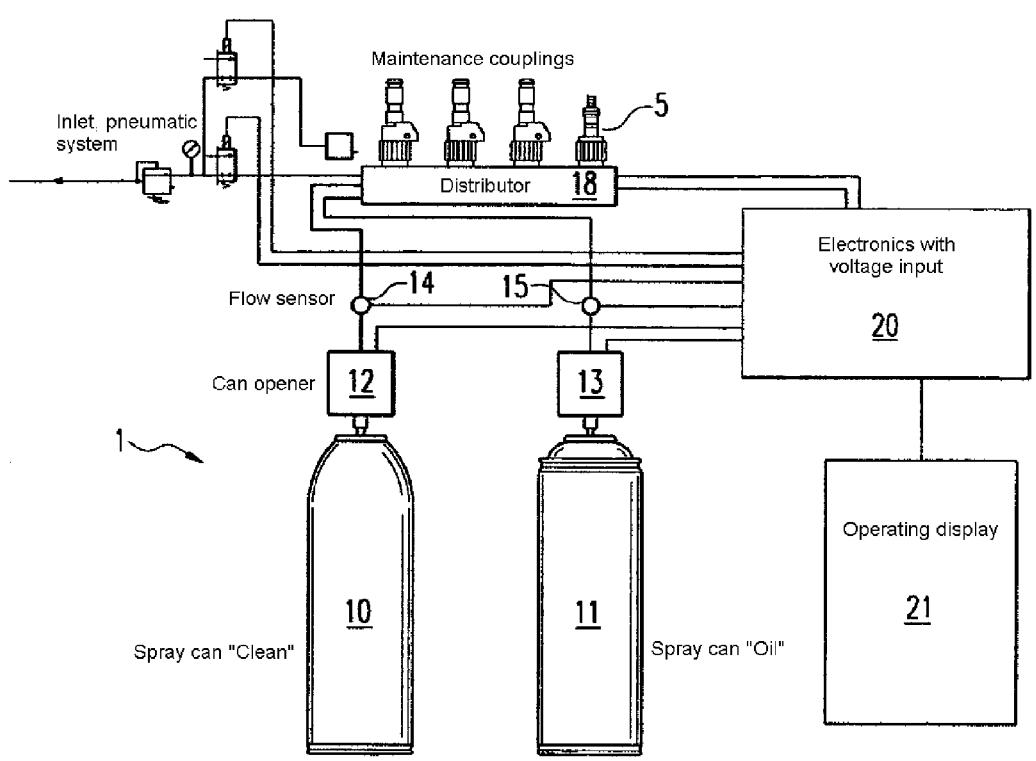
FIG. 1 shows, in schematic form, a first embodiment of a device according to the invention for disinfecting, sterilizing and/or maintaining dental instruments.

FIG. 1 first shows, in schematic form, the configuration of a first embodiment of a device according to the invention for disinfecting, sterilizing and/or maintaining medical, especially dental, instruments, the device being provided generally with the reference numeral 1 hereinbelow.

The central element of the maintenance device 1 according to the invention is a maintenance and cleaning chamber, in which the instruments to be cleaned or maintained are arranged while the process is being carried out. The arrangement of the instruments is effected by means of an instrument carrier, on which several plug-in positions or couplings 5 are arranged. Different couplings 5 are preferably provided, so that instruments with coupling systems from different manufacturers can be conditioned.

The cleaning or maintenance of the instruments is carried out in this first variant on the one hand by a cleaning agent and on the other hand by an oil maintenance agent. Both media are stored in corresponding storage containers 10 and 11, which are in the form of spray cans. They are arranged in a replaceable manner on connection means of the device 1 and can accordingly be changed as required. The connection means here comprise in particular specially configured means 12 and 13 via which the valves located at the upper side of the spray cans 10, 11 can selectively be opened (so-called can openers) in order to remove the corresponding agent. Precise metering of the medium in question is assisted by flow sensors 14 and 15, which are connected to an electronic control unit 20. This also controls a distributor unit 18 which is located at the maintenance couplings 5 and via which the corresponding medium can then be conveyed according to the intended process sequence to the individual couplings 5. The conditioning process can then be started via an operating display 21, which can be in the form of a touch screen, for example. It is further possible manually to enter the number and positions of the instruments that are to be conditioned via the display 21. Alternatively, however, it would also be conceivable to acquire that information automatically.

According to the schematic representation of FIG. 2—when all the plug-in positions 5 are occupied—the following time sequence is obtained:

The dental instruments provided for conditioning (for example handpieces and angle pieces or turbines) are positioned by the operator on the maintenance couplings 5 of the device. The conditioning operation is then started.

First of all, a cleaning agent, which is located in the first can 10, is flushed in pulses through the drive channel and the spray channels of the instruments. In that manner, proteins, saliva and other organic impurities are flushed out of the instruments. When a period of action has passed, the instrument is treated on the inside with an oil maintenance agent, which is stored in the can 11. During this operation, wear debris, which is formed by mechanical impurities, is primarily removed from the bearings, and fresh oil is provided. In order to monitor the contents of the cans during the conditioning, the flow sensors 14 and 15 mentioned above are arranged downstream of the spray cans 10, 11. In order to complete the process, excess oil and residual cleaning agent are blown out of the spray pipes and the drive channel of the instruments with compressed air.

This conditioning cycle is not carried out at the same time for all the instruments. Instead, internal cleaning of a subsequent instrument begins when the period of action for the cleaning agent begins for the preceding instrument. As a result, the corresponding media must be supplied from the storage containers to a coupling individually at a specific time, which permits more accurate and precise metering of the media. The period of action for the instruments increases, as is apparent from FIG. 2. In this manner, it is in turn ensured that the further media (oil and compressed air) are also supplied individually to the instruments.

As an alternative to the procedure described above, it would also be possible to replace the spray can containing the cleaning agent 10 with a container which contains the cleaning agent in liquid form. This would then be forced through the corresponding instruments via a pump, for example a plunger pump. The same procedure can also be adopted for the oil, which is then metered in a small amount to an air stream and carried by the air stream to the bearings of the instrument that is to be maintained.

In another preferred alternative, the cleaning agent is introduced in a metered manner in mist form into the gear and spray channel of the instrument. Atomization can be carried out by impregnation of a sinter filter, through which compressed air is subsequently blown, the mist that forms being conveyed into the instrument. During the period of action, the cleaning solution can be moved by means of further compressed-air pulses. At the end of the period of action, water is then conveyed by means of a pump, for example a magnet pump, and the gear and spray channel of the instrument is flushed. The water is then blown out by means of compressed air. The sequence can be optimized in terms of time, pulses, amount of cleaning agent and repetitions, it again being provided, however, that the cycles for the individual instruments are started in a staggered manner, that is to say each instrument is cleaned separately and consequently purposively. The same is also true for the subsequent oil maintenance, where oil is in turn introduced into the gear channel preferably atomized in the form of a mist and metering of the oil takes place, for example, via a time control. Atomization of the oil to form the mist can be carried out in the manner mentioned above; oil lubrication is also carried out for each instrument individually. Excess oil is then removed from the instrument, and the gear and spray channel is flushed with compressed air. This can also in particular be effected in a pulsed manner in order to improve the dispelling of the excess oil.

Figure 3:
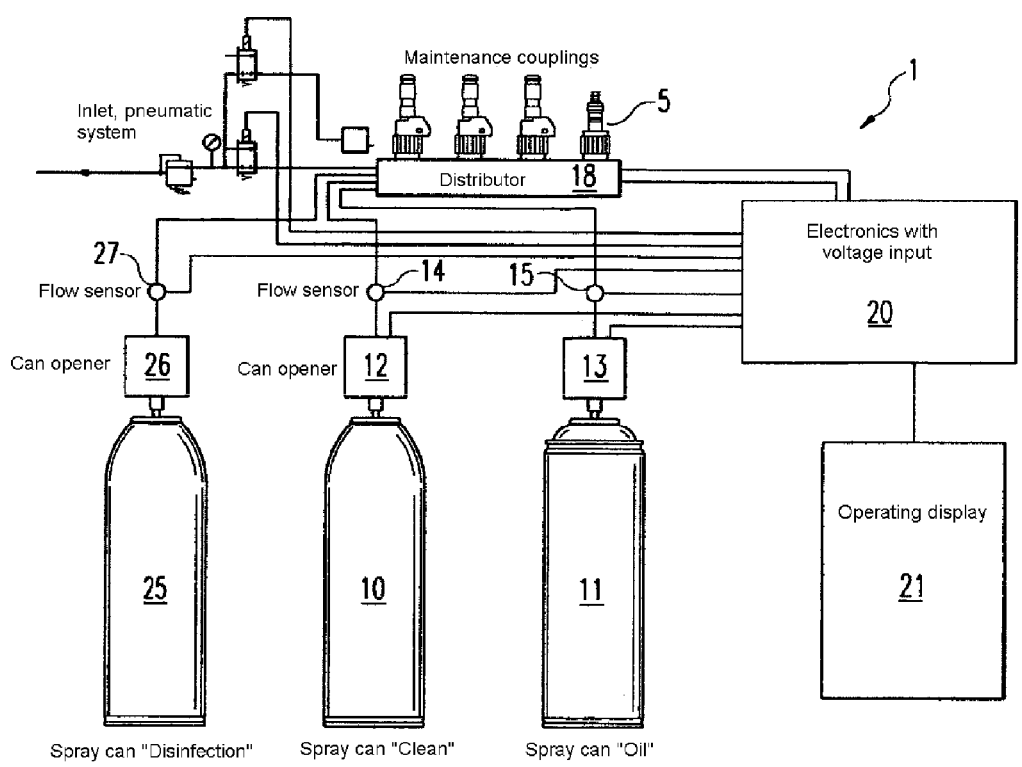
FIG. 3 shows a second embodiment of a device according to the invention for disinfecting, sterilizing and/or maintaining dental instruments.

FIG. 3 shows a further development of the device of FIG. 1, in which identical elements are provided with the same reference numerals. The device 1 of FIG. 3 differs in that disinfection of the instruments that are to be conditioned is additionally to take place. To that end, a disinfectant, which is again provided in a spray can 25, is used. The spray can 25, like the two cans 10 and 11, is arranged downstream of means for opening the valve 26 and a flow sensor 27.

The process sequence shown in FIG. 4 corresponds substantially to the sequence of FIG. 2, but in this case disinfection of the instruments takes place after the cleaning agent has been allowed to act, the corresponding disinfectant preferably being sprayed through the instruments once for three seconds. This is followed by a period of action of at least two minutes which—as shown in FIG. 4—increases for each of the individual instruments. The period of action for the cleaning agent is in this case the same for all the instruments.

Figure 5:
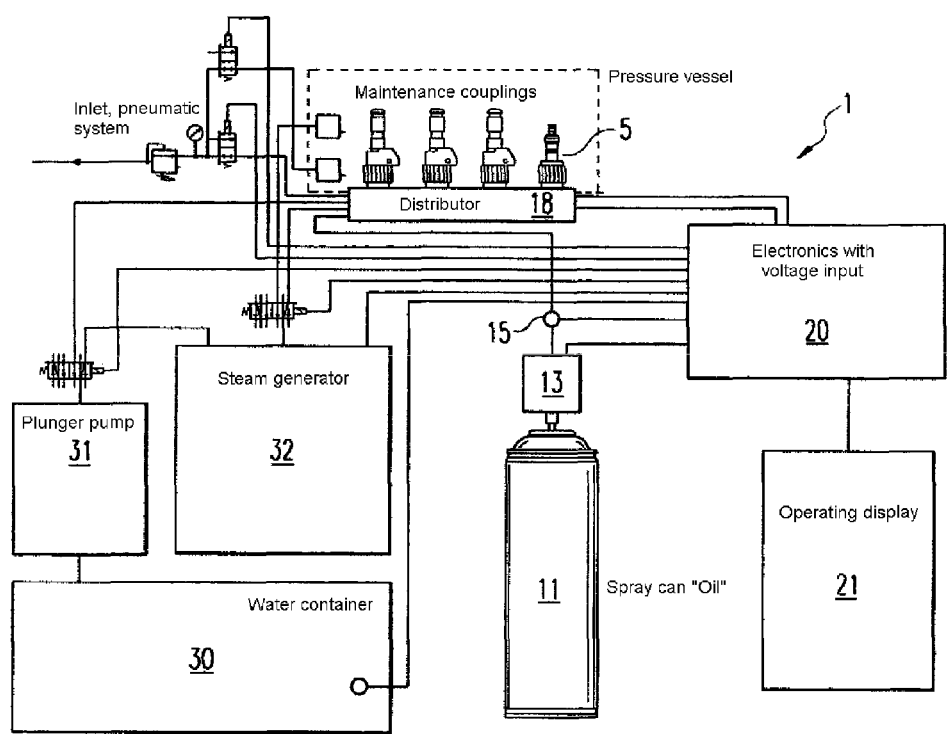
FIG. 5 shows a third embodiment of a device according to the invention for disinfecting, sterilizing and/or maintaining dental instruments.

In the third variant according to FIG. 5, it is provided that superheated steam is used for cleaning and disinfecting the instruments. Superheated steam is very energy-rich and, on account of its physical properties, also transmits heat very well and quickly, which is used in the present variant. Identical elements are again provided with the same reference numerals.

The device 1 accordingly first has a fresh water container 30, from which water, preferably demineralised water, is pumped by means of a pump 31 into a steam generator 32. In the steam generator 32, the water is heated and converted into superheated steam having a temperature of more than 120° Celsius.

After a start pulse, superheated steam then flows through the instrument that is to be conditioned, which is arranged on one of the couplings 5, for about 20 seconds. The steam flows through both the spray channels and the gear channel in order to effect internal cleaning. During this procedure, the instrument heats up to about 98° Celsius. External cleaning of the instrument is then carried out in the same manner, by spraying it with superheated steam.

As is known, the effect of disinfection is based on temperatures of about 100° Celsius. In order to make this disinfection operation more effective, the cleaning chamber of the device 1 can be sealed so that an overpressure is produced. This allows temperatures above 100° Celsius to be achieved. The disinfection time can in this case be reduced to a few seconds.

Figure 6:
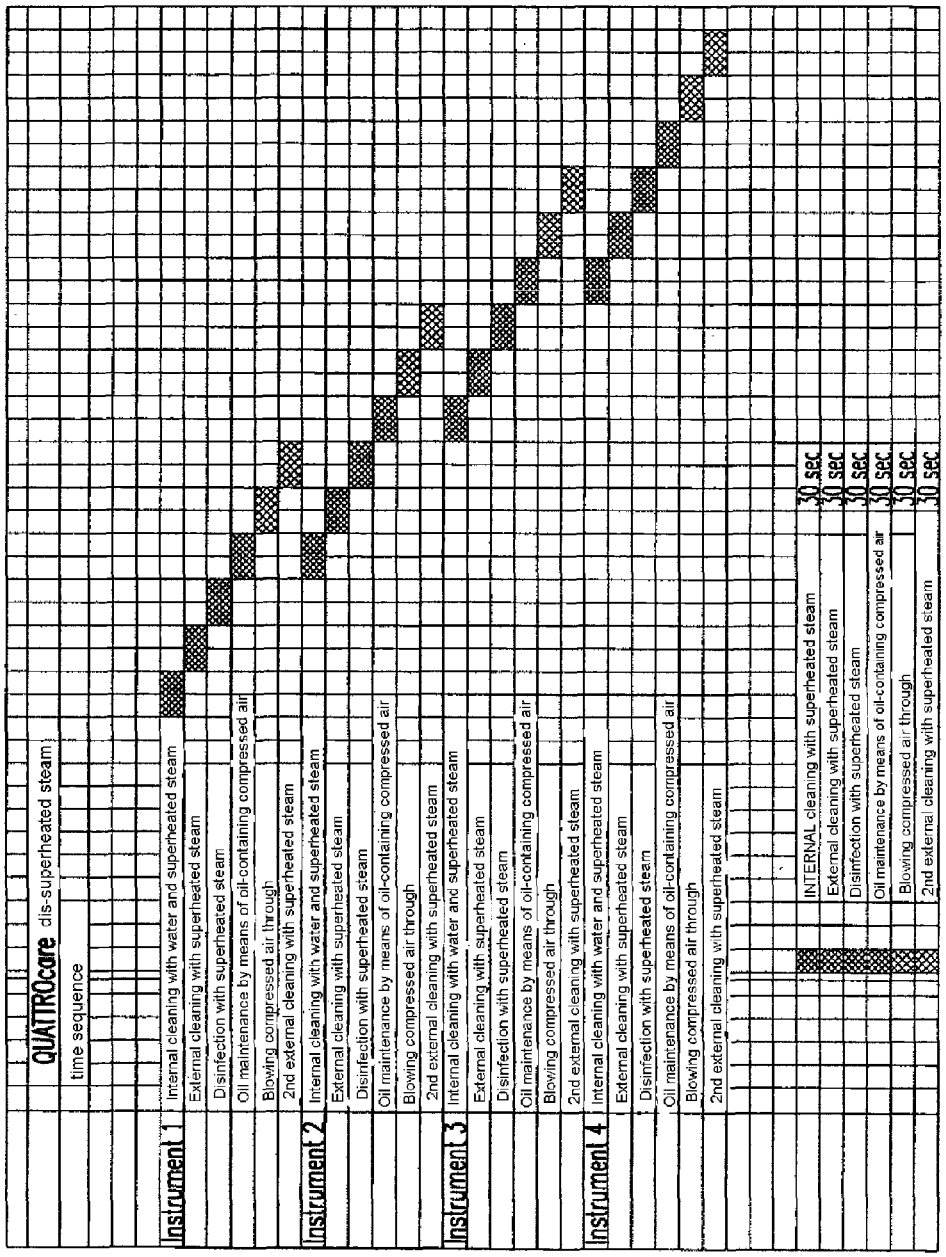
FIG. 6 shows the time sequence of the reconditioning of four instruments in the embodiment of FIG. 5.

In the next step (see FIG. 6), oil maintenance is then carried out, the oil maintenance agent, as in the variants described above, again being removed from the spray can 11 and sprayed through the instruments. The use of a spray has the further advantage that a low temperature is produced as a result of the relaxation of the propellant gas, which cools the heated instrument. Any excess oil can then be forced out of the instrument interior via the filtered compressed air. Finally, external cleaning is carried out—preferably by means of a movable annular nozzle which is guided over the instrument and which is described in greater detail below. During this operation, escaped oil in particular is cleaned from the surface of the instrument by means of superheated steam.

The conditioning cycles for the various instruments are again carried out in a staggered manner, the cycle for one instrument being started when the preceding instrument is being maintained with oil.

Figure 7:
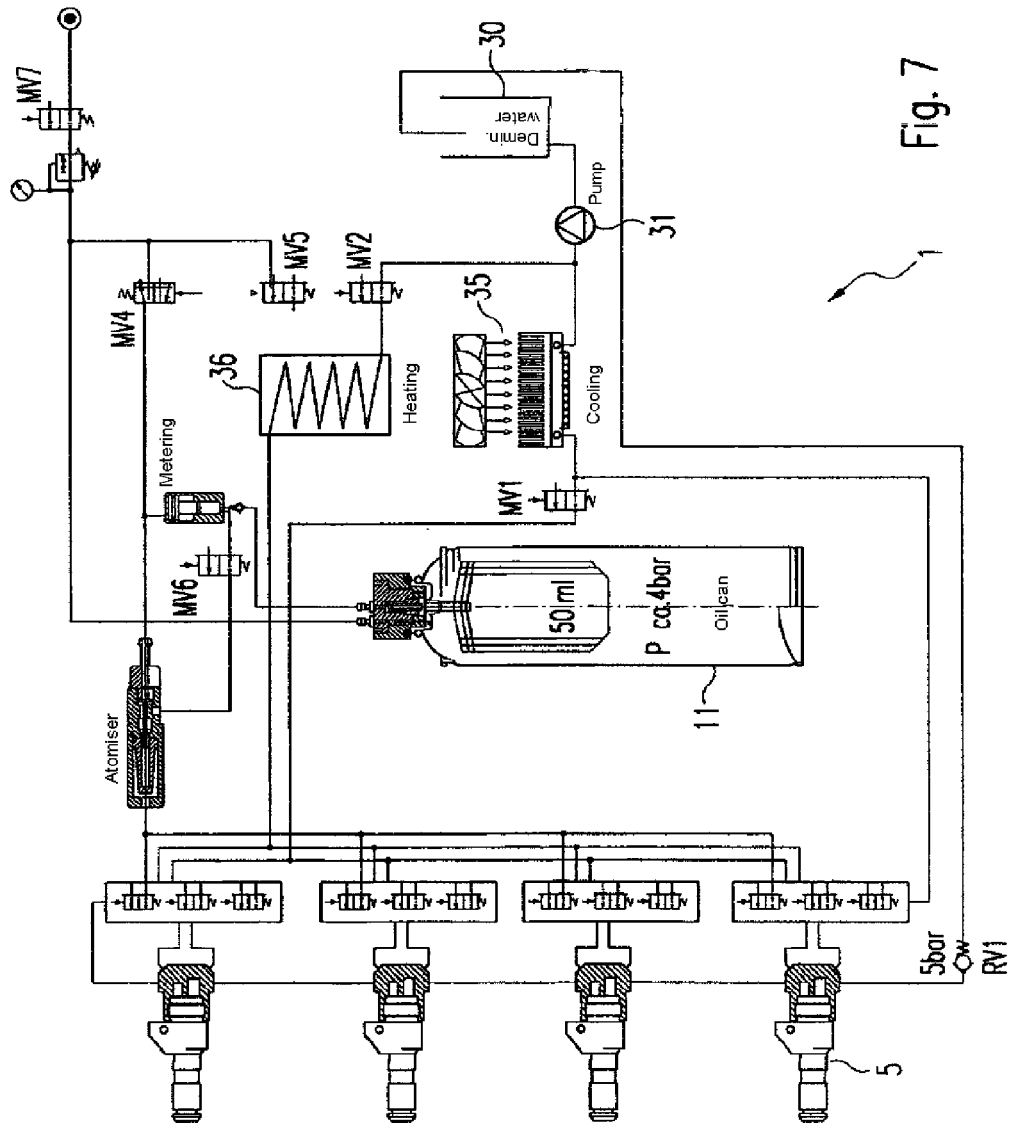
FIG. 7 shows a fourth embodiment of a device according to the invention for disinfecting, sterilizing and/or maintaining dental instruments.

A variant of the device described above is shown in FIG. 7. The advantage of this variant is thorough and rapid cleaning with a simultaneous disinfecting action.

In this device, internal cleaning of the instruments with cold water is first carried out in order to remove blood and other residues. The solenoid valve MV1 and the pump 31 are hereby activated. Cold water then flushes the instrument. The water is cooled by means of a cooling unit 35 in order to allow blood residues to be dissolved as well as possible. The pump 31 is preferably a magnet pump, which generates a high pulsed pressure. The cooling unit 35 can be in the form of, for example, a Peltier element, a compressor or a cyclone tube. The hoses or lines should be as stable as possible for good transmission of the pressure pulses. After an interval, this cycle can be repeated several times in order to increase the cleaning action.

Cleaning with cold water is followed by internal cleaning with steam in order to detach oil impurities and achieve internal disinfection. To that end, the valve MV2 is opened. By means of the pump 31, water is injected into the heating vessel 36 and converted to the vapor phase. The steam then flows through the instrument and cleans and disinfects it. The solenoid valve MV4 is then opened. Compressed air flows into the instrument and drives water out and at the same time cools it. It is also possible for oil from the storage container 11 to be added to the compressed air in order to maintain the instrument at the same time.

The various cleaning and maintenance steps for the instruments are again started in a staggered manner in order to achieve more accurate metering and hence cleaning of the instruments.

In particular when using superheated steam to clean the instruments, it is necessary to direct the cleaning agent, that is to say the superheated steam, effectively at the external surface of the instruments. This can be effected, for example, by means of a specially configured spray arm, which is shown in FIGS. 8a to 8b. The particular feature here is that the spray arm 40 rotates and can be moved in the Z-axis. Furthermore, it has several nozzles 41 to 44, from which the steam emerges. As the arm 40 rotates, steam ejection switches from the nozzle 41 to the further nozzles 42, 43 and 44. In order to be able to clean over the entire height of the instrument, either the individual nozzles 41 to 44 are moved along the instrument, or several nozzles arranged in strip form are present.

FIGS. 8b and 8c show various possibilities for arranging the nozzles, the variant in FIG. 8b having the advantage over the variant of FIG. 8c that the jet of steam strikes the instrument at from 0° to 45°. In the variant of FIG. 8c, on the other hand, the angle can even be 180°.

Finally, FIGS. 9 and 10 show a further possibility for cleaning the outside of an instrument by means of superheated steam. The fundamental constituent of this arrangement is in each case a ring 50, which is movable in all three axes. It has a plurality of contact segments as well as nozzles on its inside, from which the steam emerges. The nozzles can be rotatably mounted, for example, on an inner ring, the backward push then allowing the nozzles to rotate. The outside radius corresponds at least to the eccentricity of an angle piece.

The use of this arrangement is as follows. A corresponding arm moves the ring 50 over the instrument 100 as shown schematically in FIG. 9. The ring 50 is then subsequently lowered. If the instrument 100 is not met centrally, a switch 53 of the ring 50 triggers. It is thereby known in which direction the ring 50 is to be moved. The procedure is carried out until all the switches of the ring 50 are free. The ring 50 is then lowered further until one of the switches triggers again. During this procedure, superheated steam is sprayed continuously onto the outside of the instrument 100.

In order then to move the ring 50 to the upper side again, switches or sensors are likewise located on the upper side of the ring. Alternatively, it would also be conceivable to store the contour determined during the downward movement and traverse it again in the reverse direction for the upward movement. Ultimately, the use of this special ring 50 allows the superheated steam to be applied effectively to the instruments in order to utilize the cleaning and disinfecting property of the steam.

Figure 11A:
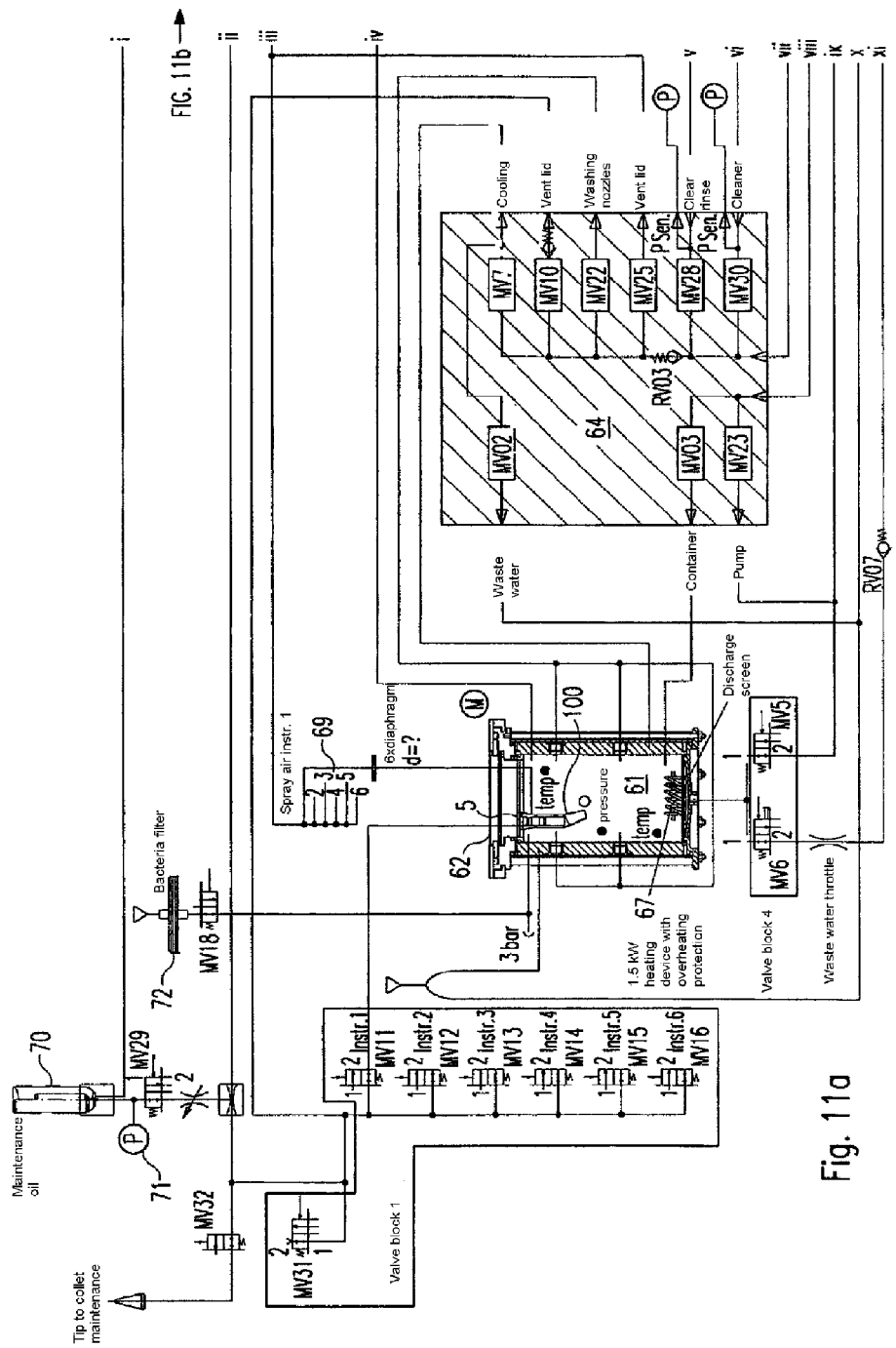
FIG. 11 shows a fifth embodiment of a device according to the invention for disinfecting, sterilizing and/or maintaining dental instruments.
Figure 11B:
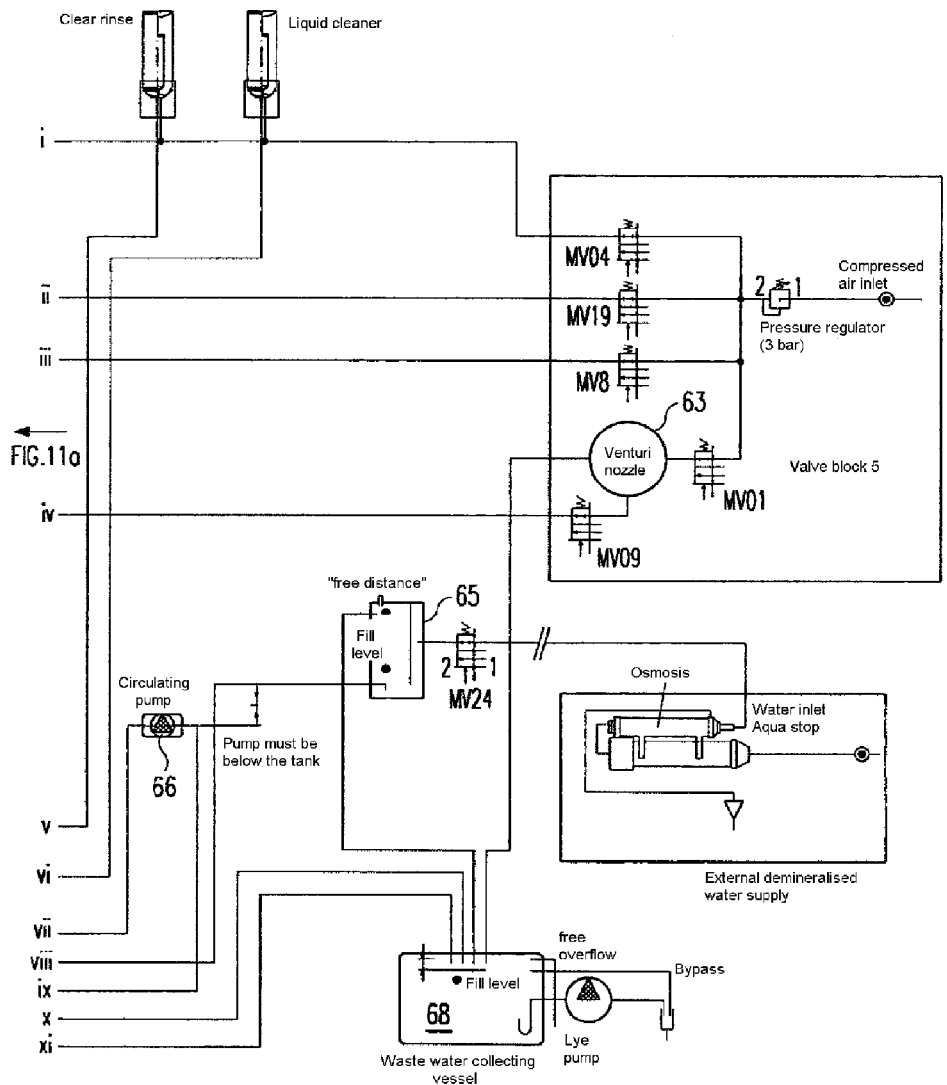

Finally, a further embodiment of a device according to the invention for disinfecting, sterilizing and/or maintaining dental instruments is to be described by means of FIGS. 11a and 11b. FIGS. 11a and 11b show the schematic construction of a device in which individual instruments are conditioned in six successive individual sections. They are in particular the following working steps: washing, oil maintenance, clear rinsing, and sterilization, drying and cooling. As explained below, each individual step can be divided into further steps. The procedure in the conditioning of the various instruments is as follows:

a) Initialization:

Reconditioning of the instruments first begins with initialization of the device. The fill levels in the various storage containers and pressures are checked and the couplings 5 in the maintenance chamber 61 are interrogated for occupancy. This is effected by passing overpressure into the maintenance chamber 61 and then opening a valve (MV 11 to MV16). The overpressure escapes into the atmosphere via the optionally occupied coupling 5 via the corresponding valve—for example MV 11—and MV31. The pressure loss in a specific time is used to determine whether the maintenance coupling 5 in question, that is to say the maintenance coupling 5 associated with the corresponding valve, is occupied or free.

b) Washing

The instruments 100 that are to be reconditioned are positioned on the carrier 62, which at the same time forms the lid of the maintenance chamber 61, which is then placed in/onto the maintenance chamber 61. By means of a motor-driven closure device, the lid is firmly connected to the maintenance chamber 61 and thereby sealed therewith. Then, with the aid of a venturi nozzle 63, a vacuum is produced in the maintenance chamber 61 and the valve MV03 leading to the chamber 61 is opened in the valve block "Water" 64. Wash water then flows from the container 65 into the maintenance chamber 61. After filling, MV03 is disconnected and the circulating pump 66 is activated. The wash water follows the path via the valves MV22, the washing nozzles, the valve MV5 back to the circulating pump 66 again. After cold external cleaning of the instruments 100, cold internal cleaning is carried out, to which end the valves MV10 and the corresponding valve of the associated maintenance coupling MV11 to MV16 are opened sequentially. The wash water in the maintenance chamber 61 is guided to the circulating pump 66 again via MV5.

After the cold washing, liquid cleaner is added to the wash water via the valve MV30 and the heating means 67 is switched on in order to heat the wash water. This warm washing is concluded by switching off the heating means 67, the circulating pump 66 and the valves MV 22, MV 10 and MV 5. Valve MV 6 is opened, and the wash water can be introduced into the waste water collecting vessel 68. The procedure of emptying can be assisted by the supply of compressed air into the maintenance chamber 61 via the valve MV 8 and the distributor unit 69. A discharge screen in the bottom of the maintenance chamber 61 prevents the ingress of coarser impurities into the pipe system.

From a programming point of view, as an alternative to the described procedure, it is also possible to carry out first internal cleaning and then external cleaning.

c) Maintenance

Oil maintenance of the instruments 100 is carried out sequentially. This in turn ensures that each instrument 100 to be maintained receives the correct amount of oil. The oil storage container 11, which is preferably in the form of a two-chamber can, is subjected to compressed air, which is effected by opening the valve MV04. The inner bag of the oil can 11, which contains the maintenance oil, is then under a corresponding external pressure. By opening the valve MV29, oil flows via the venturi nozzle into an air stream. The amount of oil is thereby dependent on the opening time of the valve MV29 and the free cross-section of the subsequent throttle. The air stream, released by opening valve MV 19, carries the oil, which is now atomized, via a solenoid valve (MV11 to MV16) connected to the instrument 100 to be maintained. If there is no longer any oil in the inner bag of the can 11, then no pressure prevails therein either. The pressure sensor 71 detects this pressure drop and, where appropriate, reports that the oil can is empty.

d) Clear Rinsing:

The subsequent step of clear rinsing is required to rinse off any oil on the surface of the maintained instruments 100 and to prevent water spots from forming on the instruments.

To this end, the maintenance chamber 61, as already described above, is filled with water. Clear rinse is metered thereto via the valve MV 28. In order to utilize the action of the clear rinse, the water is heated to about 70° C. by the heating means 67 and then rinses the instruments clear via the circulating pump and the washing nozzles. When the operation is complete, the liquid, as likewise already described, is passed out of the maintenance chamber 61 into the waste water collecting vessel 68.

e) Sterilization:

It is possible to carry out class "B" or "S" sterilization or alternatively only disinfection. The most complex process of class "B" is to be described.

In the present embodiment, the double or triple evacuation of the maintenance chamber 61 required for class "B" is achieved via the vacuum nozzle. To that end, all the valves leading to the maintenance chamber 61 are closed. Only valve MV9 is open. By subsequently opening the valve MV01, the necessary vacuum is produced in the maintenance chamber via the venturi nozzle 63. The waste air from the venturi nozzle 63 is passed into the waste water collecting vessel 68.

The steam necessary for the sterilization is generated by heating the base plate of the maintenance chamber 61 and spraying water onto the base plate. When the parameters necessary for sterilization (pressure, temperature) have been reached, this setting is kept constant for the entire sterilization time.

The pressure is then let off (into the waste water collecting vessel 68) via the valve MV6, and pressure equalization is carried out via the valve MV18 and the bacteria filter 72 arranged upstream thereof.

A sterilization process of class "S" or a disinfecting process proceeds in a similar manner, but no vacuum is produced in the case of class "B" and the temperatures are lower in the disinfecting process.

f) Drying and Cooling:

After each sterilization, the instruments 100 are wet on the inside and outside due to the steam. In order to dry the instruments 100, a condensation process is used in the present device, to which end the space between the inside chamber and the outside chamber of the maintenance chamber 61 is flooded with cold water. To that end, cold water is fed by the pump 66 via the open valve MV 23 into the space between the walls via the valve MV 7. The maintenance chamber 61 is thereby cooled and any steam in the maintenance chamber condenses on the inside wall, which is then cold. In order to assist the drying and cooling of the instruments 100, filtered compressed air can be introduced into the maintenance chamber 61 to move the air. If the space between the containers is filled with water which is heated, that warm water is fed to the waste water collecting vessel via a water line. When drying and an acceptable temperature of the instruments 100 have been reached, the reconditioning operation is complete.

Overall, therefore, the present invention provides the possibility of reconditioning dental instruments effectively and conveniently.

The invention claimed is:

1. A device for disinfecting, sterilizing and/or maintaining medical instruments, the device comprising:
    a maintenance and cleaning chamber for receiving instruments that are to be conditioned, the maintenance and cleaning chamber including one or more couplings for receiving an instrument and a rotating element with nozzles for applying superheated steam to an outside of the instrument;
    a distributor connected to the one or more couplings;
    a source of steam connected to the distributor and configured to produce superheated steam;
    a source of maintenance oil connected to the distributor; and
    an electronic control unit operatively connected to the distributor, to the source of steam, and to the source of maintenance oil, the electronic control unit being configured to execute a conditioning cycle for each instrument attached to the one or more couplings, the conditioning cycle for each instrument including sequentially executing an internal cleaning phase with superheated steam, a first external cleaning phase with superheated steam, a disinfection phase with superheated steam, an oil maintenance phase with oil-containing compressed air, an oil clearing phase by blowing compressed air through the instrument, and a second external cleaning phase with superheated steam,
    wherein the electronic control unit is operatively coupled to an opening device that is connected to the source of maintenance oil and the electronic control unit is operatively coupled to a valve that is connected to a pneumatic system, and the electronic control unit is configured to accomplish the conditioning cycle for the instrument by, supplying superheated steam from the steam source to the distributor for the internal cleaning phase, by supplying superheated steam from the steam source to the rotating element for the first external cleaning phase, by supplying superheated steam from the steam source to the maintenance and cleaning chamber for the disinfection phase, by manipulating the opening device and the valve to supply oil-containing compressed air to the distributor for the oil maintenance phase, by manipulating the opening device and the valve to supply only compressed air to the distributor and to allow the compressed air to blow through the instrument during the oil clearing phase, and by supplying superheated steam from the steam source to the rotating element for the second external cleaning phase, and
    wherein the electronic control unit is configured to stagger respective start times and respective end times for conditioning cycles for different instruments such that the disinfection phase with superheated steam of an instrument is performed simultaneously with the second external cleaning phase with superheated steam of a preceding instrument.

2. The device according to claim 1, wherein the rotating element is an arm or a ring.

3. The device according to claim 1, wherein the one or more couplings are configured to receive dental instruments.

4. The device according to claim 1, further comprising a flow sensor operatively connected to the source of maintenance oil and to the electronic control unit, the electronic control unit receiving flow information from the flow sensor and using the flow information to control the opening device to meter the maintenance oil to the distributor.

* * * * *